United States Patent
Zheng et al.

(10) Patent No.: US 9,330,461 B2
(45) Date of Patent: May 3, 2016

(54) IMAGE-BASED METHOD FOR MEASURING ELASTICITY OF BIOLOGICAL TISSUES AND SYSTEM THEREOF

(75) Inventors: Hairong Zheng, Guangdong (CN); Lili Niu, Guangdong (CN); Ming Qian, Guangdong (CN)

(73) Assignee: Shenzhen Institutes of Advanced Technology Chinese Academy of Sciences, Guangdong (CN)

( * ) Notice: Subject to any disclaimer, the term of this patent is extended or adjusted under 35 U.S.C. 154(b) by 71 days.

(21) Appl. No.: 14/233,193

(22) PCT Filed: Aug. 29, 2012

(86) PCT No.: PCT/CN2012/080732
§ 371 (c)(1),
(2), (4) Date: Jan. 16, 2014

(87) PCT Pub. No.: WO2013/029546
PCT Pub. Date: Mar. 7, 2013

(65) Prior Publication Data
US 2014/0147028 A1    May 29, 2014

(30) Foreign Application Priority Data
Sep. 1, 2011    (CN) .......................... 2011 1 0257166

(51) Int. Cl.
*G06K 9/00* (2006.01)
*G06T 7/00* (2006.01)
(Continued)

(52) U.S. Cl.
CPC .......... *G06T 7/0014* (2013.01); *A61B 5/02007* (2013.01); *A61B 6/5217* (2013.01);
(Continued)

(58) Field of Classification Search
USPC ........................................................ 382/131
See application file for complete search history.

(56) References Cited

U.S. PATENT DOCUMENTS 6,283,917 B1 * 9/2001 Jago et al. ..................... 600/437
2010/0016724 A1   1/2010 Arai et al.
(Continued)

FOREIGN PATENT DOCUMENTS

| CN | 15866408 A | 3/2005 |
| CN | 101553174 A | 10/2009 |

(Continued)

OTHER PUBLICATIONS

Niu et al, "Ultrasonic particle image velocimetry for improved flow gradient imaging: algorithms, methodology and validation", Physicas in Medicine and Biology, Mar. 19, 2010, pp. 2103-2120.*
(Continued)

*Primary Examiner* — Yon Couso
(74) *Attorney, Agent, or Firm* — Rosenberg, Klein & Lee

(57) ABSTRACT

The present disclosure proposes an image-based method for measuring elasticity of biological tissues including following steps: obtaining N successive grayscale images of a testing biological tissue, where N is a positive integer; obtaining regions of interest (ROI) of the grayscale images; dividing the regions of interest into a grid of small sections; calculating relative displacement vector of each interrogation window using texture matching method; and calculating elastic modulus of each interrogation window according to the relative displacement vectors. The present disclosure also proposes an image-based system for measuring elasticity of biological tissues. The present disclosure applies to various resolutions of grayscale images obtaining in ultrasound imaging, optical imaging, photoacoustic imaging, CT imaging, magnetic resonance imaging ect. The system can be integrated into a traditional clinical imaging system as an image post-processing software module to characterize tissue elasticity. Because it's no need to update the traditional clinical imaging system hardware, updating cost is low. It's easy to be accepted by hospital and is convenient to popularize.

7 Claims, 11 Drawing Sheets

(51) Int. Cl.

| | |
|---|---|
| *G01N 33/483* | (2006.01) |
| *A61B 8/08* | (2006.01) |
| *A61B 5/02* | (2006.01) |
| *A61B 6/00* | (2006.01) |
| *G01S 7/52* | (2006.01) |
| *G06T 7/20* | (2006.01) |
| *A61B 6/03* | (2006.01) |
| *A61B 5/00* | (2006.01) |
| *A61B 8/00* | (2006.01) |

(52) U.S. Cl.
CPC ............... *A61B8/0891* (2013.01); *A61B 8/485* (2013.01); *G01N 33/4833* (2013.01); *G01S 7/52042* (2013.01); *G06T 7/0012* (2013.01); *G06T 7/2013* (2013.01); *A61B 5/0037* (2013.01); *A61B 6/03* (2013.01); *A61B 8/587* (2013.01); *G06T 2207/20021* (2013.01); *G06T 2207/30024* (2013.01)

(56) References Cited

U.S. PATENT DOCUMENTS

| | | | |
|---|---|---|---|
| 2010/0106018 | A1 | 4/2010 | Jiang et al. |
| 2011/0206262 | A1* | 8/2011 | Sammak et al. ............... 382/133 |
| 2014/0147028 | A1 | 5/2014 | Zheng et al. |

FOREIGN PATENT DOCUMENTS

| | | |
|---|---|---|
| CN | 101569543 A | 11/2009 |
| CN | 102423264 A | 4/2012 |

OTHER PUBLICATIONS

CN1586408, "Multile size biological tissue displacement evaluating method", Mar. 2, 2005, pp. 1-6 (translated).*

Niu, et al.; "Ultrasonic particle image velocimetry for improved flow gradient imaging: algorithms, methodology and validation"; Phys Med Biol. Apr. 7, 2010; 55(7):2103-2120.

* cited by examiner

IMAGE-BASED METHOD FOR MEASURING ELASTICITY OF BIOLOGICAL TISSUES AND SYSTEM THEREOF

FIELD OF THE INVENTION

The present disclosure relates generally to elastography technologies, and more particularly to an image-based method for measuring elasticity of biological tissues, and an image-based system for measuring elasticity of biological tissues.

BACKGROUND OF THE INVENTION

An elastic tissue in the biology body is composed by different compositions. A vessel wall, for example, is mainly composed by collagen fibers, elastins and smooth muscle cells, elastic modulus of these compositions are quite different from each other. If an accurate distribution map showing elastic modulus of a two-dimensional vessel wall can be obtained, compositions of the vessel wall can be distinguished, and the composition distributions of the vessel wall can be obtained. For an atherosclerotic plaque, the composition distributions of lipids, blood clots, fiber tissues, calcified tissues and so on can be obtained.

SUMMARY OF THE INVENTION

It is an object of the present disclosure to provide a non-invasive method for measuring elasticity of biological tissue accurately.

An image-based method for measuring elasticity of biological tissues including following steps: step A, obtaining continuous N frames of grayscale images of a testing biological tissue, where N is a positive integer; step B, obtaining regions of interest (ROI) of the grayscale images; step C, dividing the region of interest into a grid of small sections known as interrogation windows; step D, calculating relative displacement vectors of each interrogation window positioned between two successive frames using texture matching method; and step E, calculating elastic modulus corresponding to each interrogation window according to the gradient of the relative displacement vectors.

In a preferred embodiment, the successive N frames of grayscale images are collected by an imaging system, and N is a number of image frames collected by the imaging system within m complete cardiac cycles, where in is a positive integer.

In a preferred embodiment, the texture matching method further includes following steps: step D1, the two-dimensional (2-D) normalized cross-correlation technique, which combines the sub-pixel method and the filter and interpolation method, is used to calculate the two-dimensional translational displacement of the texture of each interrogation window. step D2, a multiple iterative algorithm uses the gradient of the two-dimensional translational displacement to estimate rotation and deformation. step D3, the 2-D normalized cross-correlation technique is applied with a reduced interrogation window to obtain higher spatial resolution and a spurious vector elimination algorithm is used to obtain more accurate displacement estimates. The lateral and axial components of all displacement vectors are stored in three-dimensional (3-D) arrays, where the three dimensions are lateral and axial positions within an image and frame number.

In a preferred embodiment, the tissue is a vessel wall; the step E further includes following steps: step E1, from the estimated axial displacement, a displacement gradient (strain) of each layer with a constant thickness is obtained; step E2, obtaining the maximum strain of each layer during one cardiac cycle; step E3, obtaining the elastic modulus according to the maximum strain and the blood pressure applied normal to each layer.

In a preferred embodiment, the method also includes following steps: for histochemical analysis, the tissues were sliced into sections using a microtome; the sections were stained to obtain the compositions of the tissue; the range of the elastic modulus of the different tissue compositions was acquired.

Furthermore, it is another object of the present disclosure to provide a non-invasive system for measuring elasticity of biological tissue accurately.

An image-based system for measuring elasticity of biological tissues including: a grayscale image module for obtaining a cineloop consisting of N images of a testing biological tissue, where N is a positive integer; a region of interest module for obtaining regions of interest in the grayscale images; a dividing interrogation window module for dividing the regions of interest into a grid of small sections; a relative displacement vectors module for calculating relative displacement vectors of each interrogation window using texture matching method; and an elastic modulus module for calculating elastic modulus of each interrogation window according to the gradient of the relative displacement vectors.

In a preferred embodiment, the grayscale image module is an imaging system, a cineloop consisting of N images is collected by an imaging system, and N is the number of image frames collected by the imaging system within m complete cardiac cycles, where m is a positive integer.

In a preferred embodiment, the relative displacement vectors module includes: a translational displacement module for obtaining two-dimensional translational displacement of the texture of each interrogation window using two-dimensional normalized cross-correlation technique, sub-pixel method and filter interpolation method; a geometric transformation displacement module using a multiple iterative algorithm to calculate rotation and deformation according to the gradient of the two-dimensional translational displacements; a spurious vector elimination module for obtaining more accurate displacement estimates.

In a preferred embodiment, the elastic modulus module includes: a displacement gradient (strain) calculating module for obtaining the displacement gradient of each layer with a constant thickness from the estimated axial displacement; a maximum strain calculating module for obtaining the maximum strain of each layer during one cardiac cycle; an elastic modulus obtaining module for obtaining the elastic modulus according to the maximum strain and the blood pressure applied normal to each layer.

The image-based system for measuring elasticity of biological tissues and method using the same are non-invasive and accurate, and apply to various resolutions of grayscale images obtaining in ultrasound imaging, optical imaging, photoacoustic imaging, computed tomography imaging, magnetic resonance imaging and so on. The system can be integrated into a traditional clinical imaging system as an image post-processing software module to characterize tissue elasticity. Because it's no need to update the traditional clinical imaging system hardware, updating cost is low. It's easy to be accepted by hospital and is convenient to popularize.

DETAILED DESCRIPTION OF THE EMBODIMENTS

The detailed description of the present invention will be discussed in the following embodiments.

The First Embodiment

Figure 1:
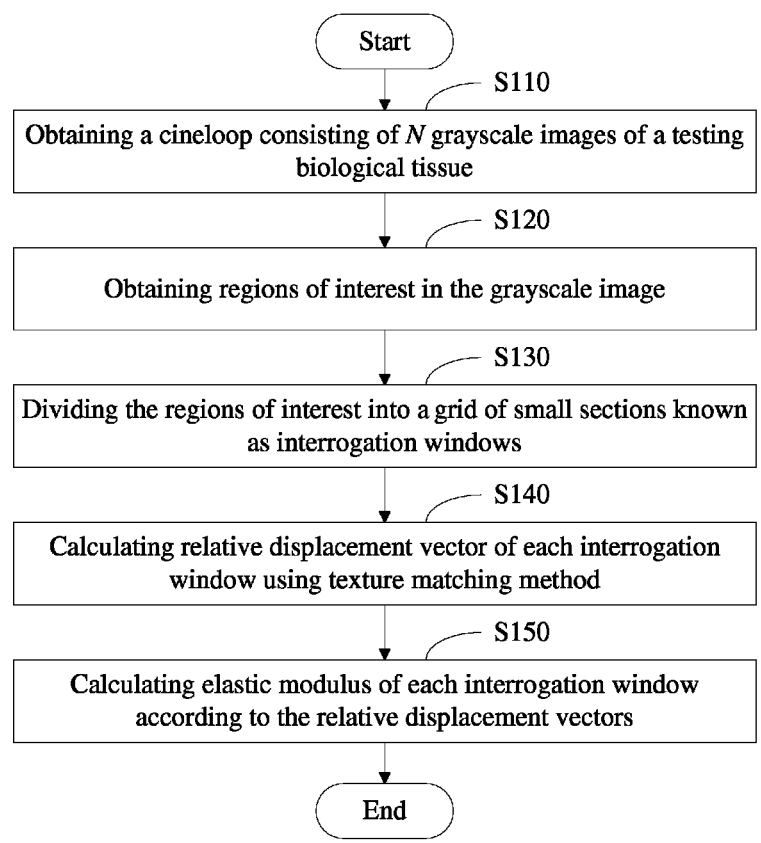
FIG. 1 is a flow chart of an image-based method for measuring elasticity of biological tissues in accordance with the first embodiment of the present disclosure.

FIG. 1 is a flow chart of an image-based method for measuring elasticity of biological tissues with the first embodiment of the present disclosure, the method includes following steps:

S110, obtaining N successive frames of grayscale images of a testing biological tissue.

The grayscale images can be obtained in various imaging technologies such as ultrasound imaging, optical imaging, photoacoustic imaging, CT imaging, magnetic resonance imaging and so on. In this embodiment, the grayscale images are obtained by an ultrasound imaging system.

N is the number of image frames which should cover at least one cardiac cycle images. For example, when the frame rate (FR) is 100 Hz, and the cardiac cycle Tc is 1 second, N=m×FR×Tc=100 m, where in is the number of the cardiac cycles, m=1, 2, 3 .... When m=1, N is an integer multiples of 100.

S120, obtaining regions of interest in the grayscale images. The regions of interest can be selected by an operator, or it can also be obtained automatically by some traditional image segmentation techniques.

S130, dividing the region of interest into a grid of small sections. The region of interest is divided into a grid of small sections known as interrogation windows with the same size, the interrogation windows are numbered sequentially starting from k1.

S140, calculating relative displacement vectors of each interrogation window positioned between two successive frames using texture matching method.

For example, the relative displacement vector positioned between the first frame and the second frame in the N frames of the interrogation window k1 is calculated using texture matching method. In this embodiment, m=1, it further includes following steps:

Step 1, two-dimensional normalized cross-correlation technique, which combines the sub-pixel method and the filter and interpolation method, is used to calculate the translational displacement of the interrogation window k1 between the first frame and the second frame. The normalized cross-correlation function corrected for the average values is used as the preferred matching criterion. It is defined as:

$$R(p, q) = \frac{\sum_{x=1}^{M_1} \sum_{y=1}^{N_1} (h(x, y)\overline{h})(k(x+p, y+q)\overline{k})}{\delta_h \delta_k}$$

where h and k denote the gray intensity distribution over an interrogation window of size $M_1 \times N_1$. $\overline{h}$ and $\overline{k}$ are the average values of the functions h and k respectively, and $\sigma_h$, and $\sigma_k$ are their standard deviations.

Since the image intensity consists of the discrete function in pixel units, the displacement vector is also in pixel units. Sub-pixel method for improving the accuracy of measurement has been developed, in which a sub-pixel displacement can be estimated by the Gaussian peak fitting formula:

$$\begin{cases} \Delta x = i + \dfrac{\ln(R_{pq}(i-1, j)) - \ln(R_{pq}(i+1, j))}{2\ln(R_{pq}(i-1, j)) - 4\ln(R_{pq}(i, j)) + 2\ln(R_{pq}(i+1, j))} \\ \Delta y = j + \dfrac{\ln(R_{pq}(i, j-1)) - \ln(R_{pq}(i, j+1))}{2\ln(R_{pq}(i, j-1)) - 4\ln(R_{pq}(i, j)) + 2\ln(R_{pq}(i, j+1))} \end{cases}$$

$R_{pq}(i,j)$ is the maximum cross-correlation function. i and j are the corresponding coordinates when the cross-correlation function obtain the maximum value. $R_{pq}(i\ 1, j)$, $R_{pq}(i+1, j)$, $R_{pq}(i, j\ 1)$ and $R_{pq}(i, j+1)$ are cross-correlation functions around four nearest grid point.

For the filter interpolation method, median filtering and bilinear interpolation are used, the formula is:

$$\begin{cases} U(x, y) > \text{median}(U(x-1:x+1, y-1:y+1)) + \\ \quad \text{threshold} * std(U(x-1:x+1, y-1:y+1)) \\ U(x, y) < \text{median}(U(x-1:x+1, y-1:y+1)) - \\ \quad \text{threshold} * std(U(x-1:x+1, y-1:y+1)) \end{cases}$$

$$U(x, y) = (1-x)(1-y)U(x-1, y-1) + $$
$$x(1-y)U(x+1, y-1) + (1-x)yU(x-1, y+1) + xyU(x+1, y+1)$$

U=(u, v) is a two-dimensional translational displacement vector.

Step 2, a multiple iterative algorithm uses the gradient of the two-dimensional translational displacement to estimate rotation and deformation.

Considering the rotation and the deformation of the tissue, Taylor series is introduced:

$$U(r) = U(r_0) + \left(\frac{\partial U}{\partial r}\right)_{r=r_0}(r-r_0) + \frac{1}{2!}\left(\frac{\partial^2 U}{\partial r^2}\right)_{r=r_0}(r-r_0)^2 + o(r-r_0)^3$$

where $$r = (x, y)$$

$$r \in \left[r_0 - \frac{1}{2}W, r_0 + \frac{1}{2}W\right],$$

$r_0$ denotes the centre of the interrogation window W.

The specific process of the iterative algorithm is: First, setting the number of iterations K (K is generally 2 or 3). Then, for an iteration number k, the windows are translated and deformed according to the displacement field $U_{k-1}$ calculated in the previous iteration k−1.

The displacement gradients U' are obtained through a centered finite difference scheme. For each correlation window, the algorithm rebuilds two new gray intensities functions f(r) and g(r) of two interrogation windows extracted from the first and second frames, where r=(x, y).

$$f(r) = f\left(r - \frac{U_{k-1}}{2} - \frac{U'_{k-1}r}{2}\right)$$

$$g(r) = g\left(r + \frac{U_{k-1}}{2} + \frac{U'_{k-1}r}{2}\right)$$

The value of the gray intensities f(r) and g(r) between pixels is obtained by bilinear interpolation between the four neighboring values. A correlation function of these new intensities is calculated by sub-pixel Gaussian peak fitting formula and the location $R_{max}$ of its peak is determined to sub-pixel accuracy. The new displacement ($U_k$ is then given:

$$U_k = U_{k-1} + R_{max}$$

Step 3, the 2-D normalized cross-correlation technique is applied with a reduced interrogation window to obtain higher spatial resolution and a spurious vector elimination algorithm is used to obtain more accurate displacement estimates.

The spurious vector elimination algorithm is based on continuity equation. According to the initial vector distribution, the allow value is set up. The following formula is applied for the spurious vector analysis:

$$val = \frac{\sum |u_{x-1:x+1, y-1:y+1} - u_{x,y}| + \sum |v_{x-1:x+1, y-1:y+1} - v_{x,y}|}{\sum |u_{x-1:x+1, y-1:y+1}| + \sum |v_{x-1:x+1, y-1:y+1}|}$$

where $u_{x,y}$ and $v_{x,y}$, can be obtained by application Gaussian templates:

$$\begin{cases} u_{x,y} = \dfrac{u_{x-1,y+1} + 2u_{x,y+1} + u_{x+1,y+1} + 2u_{x-1,y} + 2u_{x+1,y} + u_{x-1,y-1} + 2u_{x,y-1} + u_{x+1,y-1}}{12} \\ v_{x,y} = \dfrac{v_{x-1,y+1} + 2v_{x,y+1} + v_{x+1,y+1} + 2v_{x-1,y} + 2v_{x+1,y} + v_{x-1,y-1} + 2v_{x,y-1} + v_{x+1,y-1}}{12} \end{cases}$$

If the val value is smaller than the allow value, the vector unchanged. If the val value is greater than the allow value, the val should be corrected with the following formula:

$$u_{x,y} = \frac{\sum u_{x-1:x+1, y-1:y+1}}{8}$$

$$v_{x,y} = \frac{\sum v_{x-1:x+1, y-1:y+1}}{8}$$

Thus accurate relative displacement vectors u and v are obtained.

Figure 2:
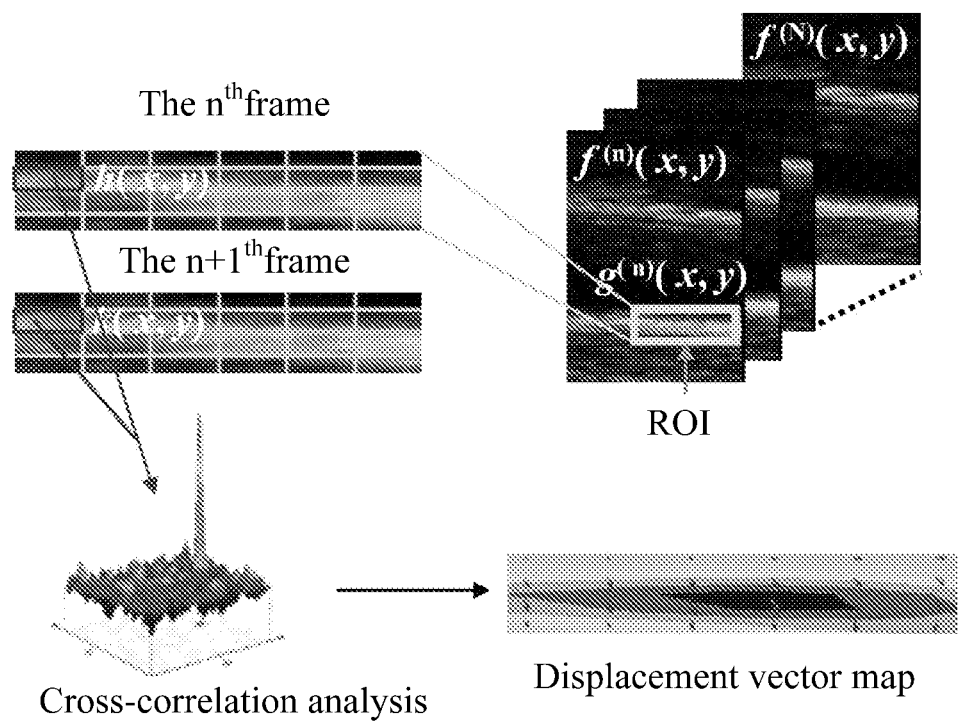
FIG. 2 is a block diagram of the texture matching method to measure the displacement for one interrogation window before and after movement.

Similarly, relative displacement vectors of other interrogation windows k2, k3 . . . are calculated in order. As shown in FIG. 2, the distribution of displacement vectors can be obtained. When m>1, relative displacement vectors in each cardiac cycle should be calculated respectively.

After calculating the distribution of displacement vectors between the first frame and the second frame, the displacement vectors between the second frame and the third frame are calculated, until the (N−1)$^{th}$ frame and the N$^{th}$ frame.

S150, calculating elasticity modulus corresponding to each interrogation window according to the gradient of the relative displacement vectors. If m>1, an average value of the m elastic modulus is calculated.

The above mentioned image-based method for measuring elasticity of biological tissues include not only the arterial wall, but also heart, lung, atherosclerotic plaque, tumor, and elastic objects (e.g. a silicone tube).

In another embodiment, the image-based method for measuring elasticity of biological tissues further includes following steps:

S162, slicing the tissue into a section and pathology staining the section. The tissue is sliced into the section using a microtome, then the section is put on a piece of glass, a stain is dropped on the section to make them contact fully in 3-5 minutes.

S164, obtaining a composition distribution of the tissue according to the results of the pathology stain. Different composition will be dyed in different color, thus the stained image can be obtained.

S166, obtaining the range of the elastic modulus corresponding to each composition according to the elastic modulus calculated in S150 and the composition distributions, including following steps: from the stained image, we know the compositions of each interrogate window. The elastic modulus of each interrogate window is assigned in the distribution of elasticity. From the histogram of elastic modulus for each interrogate window, the elasticity for each composition is obtained.

For example, after the measurement of atherosclerosis plaque, the range of elastic modulus of the different composition is: lipids (81±40 kPa), blood clots (95±56 kPa), fibrous tissue (1.0±0.63 MPa), calcified tissue (2.0±1.2 MPa).

After obtaining the range of the elastic modulus of the composition, a table of composition-elastic modulus can be created. When the elastic modulus is obtained, the composition can be obtained according to the table of composition-elastic modulus.

The Second Embodiment

The second embodiment is an embodiment using the image-based method for measuring elasticity of biological tissues, such as the common carotid arteries of volunteers.

Subjects were placed in a supine position with the head rotated 45° to the left using a 45° head pillow. The common carotid arteries were imaged in longitudinal section to enable calculation of both axial and lateral movements using an ultrasound imaging system. The grayscale images were continuously acquired over a few cardiac cycles.

Figure 3:
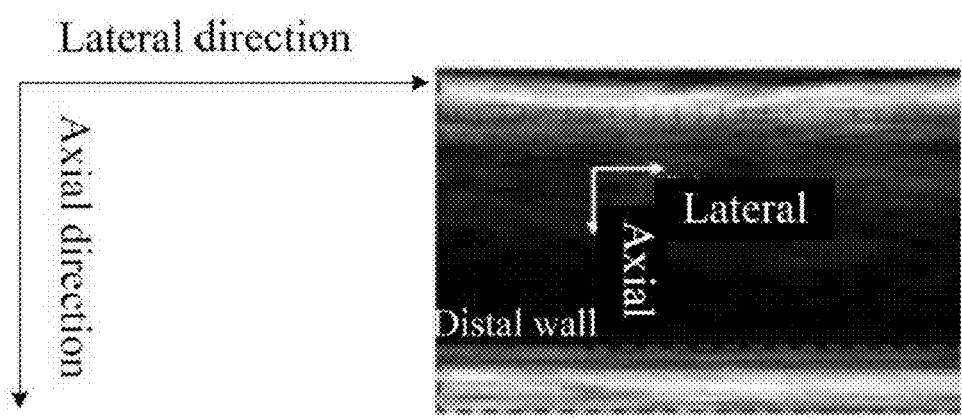
FIG. 3 is an ultrasound B-mode image of a common carotid artery of a volunteer in accordance with the second embodiment of the present disclosure.

FIG. 3 is an ultrasound B-mode image of a common carotid artery of the volunteer in accordance with the second embodiment of the present disclosure and the rectangle indicates the region of interest (distal wall). A sequence of 2-D ultrasound B-mode images were acquired at a frame rate of 223 Hz using 128 ultrasound beams with a focal depth of 10 mm and field of view of 28 mm (depth) by 25 mm (width). In this embodiment, B-mode images are continuously acquired over two cardiac cycles. A final interrogation window of 16×8 (pixels) is used with an to overlap ratio of 0.5 for the texture matching analysis.

From the estimated axial displacement v(x, y, n), the displacement gradient (strain) of each layer with a constant thickness of $h_0$ is obtained as follows:

$$\Delta\epsilon_{max}(x,y,n)=(v(x+1,y,n)-v(x,y,n))/h_0$$

The maximum strain of each layer during one cardiac cycle is obtained by $\Delta\epsilon(x,y)=\max_n |\Delta\epsilon(x,y,n)|$. Assuming that the arterial wall is incompressible and the blood pressure is applied normal to each layer, the elastic modulus, E(x, y), is approximately given:

$$E(x, y) = \frac{1}{2}\left(\frac{R_{il}}{h_0 \cdot L} + \frac{L-x+1}{L}\right)\frac{\Delta P}{\Delta\epsilon_{max}(x, y)}$$

where L and $R_{il}$ are the number of layers and the inner radius of the l-th layer, respectively. $\Delta P$ is blood pressure measured at the brachial artery.

Figure 4:
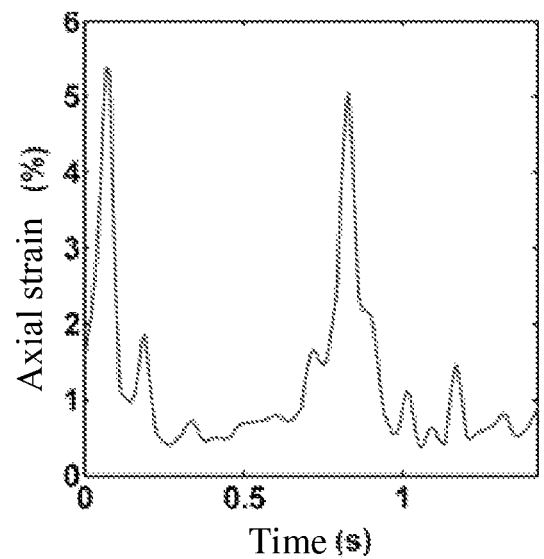
FIG. 4 is axial strain profiles computed over the region of interest (distal wall) shown in FIG. 3 exhibiting a periodic pattern following the cardiac cycle.
Figure 5:
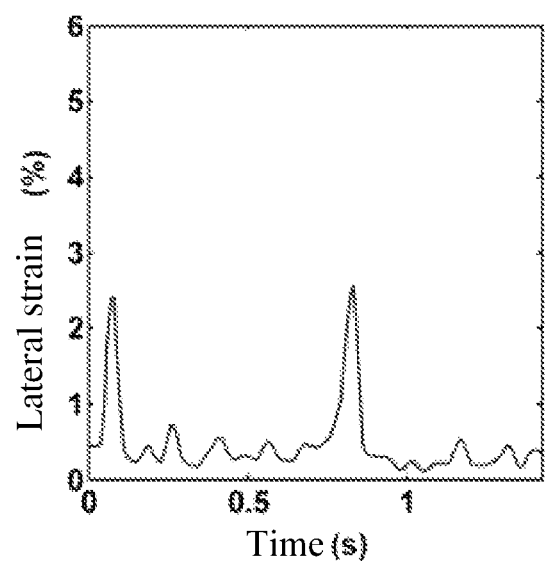
FIG. 5 is lateral strain profiles computed over the region of interest (distal wall) shown in FIG. 3 exhibiting a periodic pattern following the cardiac cycle.

FIG. 4 is axial strain profiles computed over the region of interest (distal wall) shown in FIG. 3 exhibiting a periodic pattern following the cardiac cycle. FIG. 5 is lateral strain profiles computed over the region of interest (distal wall) shown in FIG. 3 exhibiting a periodic pattern following the cardiac cycle.

The Third Embodiment

Figure 6:
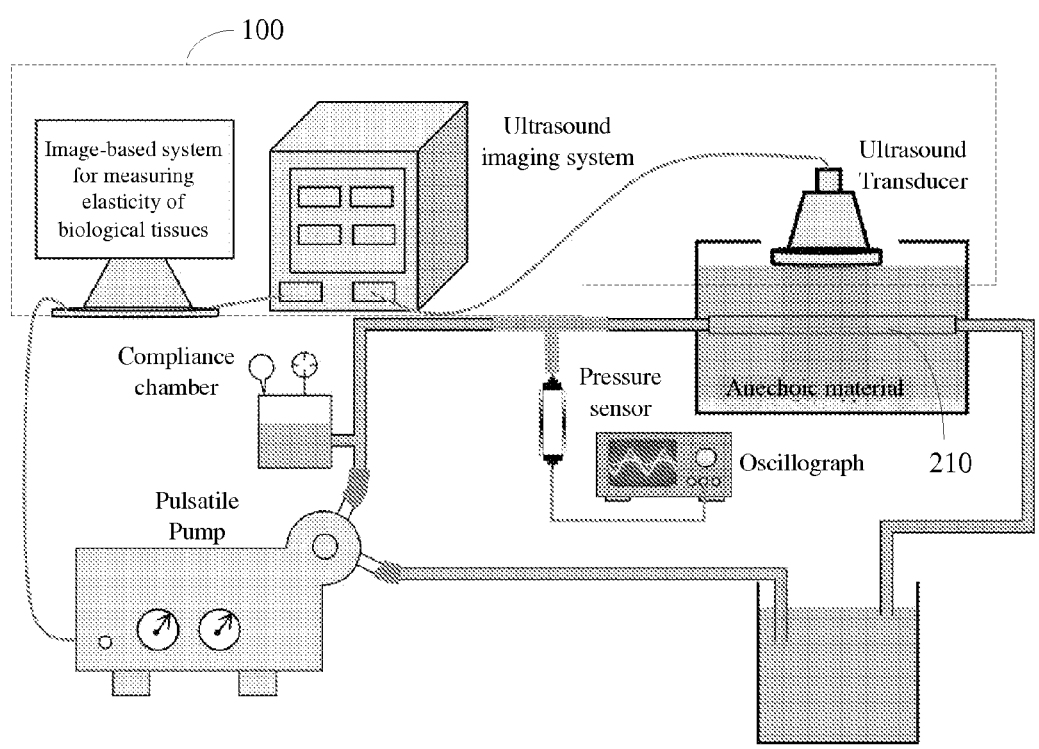
FIG. 6 is experimental set-up used to measure the elastic modulus of an in vitro arterial phantom using the texture matching method in accordance with the third embodiment of the present disclosure.

FIG. 6 is experimental set-up used to measure the elastic modulus of in vitro arterial phantom using the texture matching method in accordance with the third embodiment of the present disclosure. The system 100 includes an ultrasound transducer, an ultrasound imaging system, and an image-based system for measuring elasticity of biological tissues. The ultrasound imaging system is used to capture the B-mode images, and sending the image to the image-based system for measuring elasticity of biological tissues.

Pulsatile pressure was created with a pulsatile pump (Model 55-3305) and a compliance chamber was used to serve as a cushioning function. A pressure sensor (HDP708) was placed between the pump and the arterial phantom 210 to measure the intraluminal pressure. The arterial phantom 210 is placed in a large tank. An acoustic pad was placed under the hard plastic pipe to prevent strong acoustic reflection from the bottom of the tank. The arterial phantom 210 in this embodiment is a silicone tube.

Figure 7:
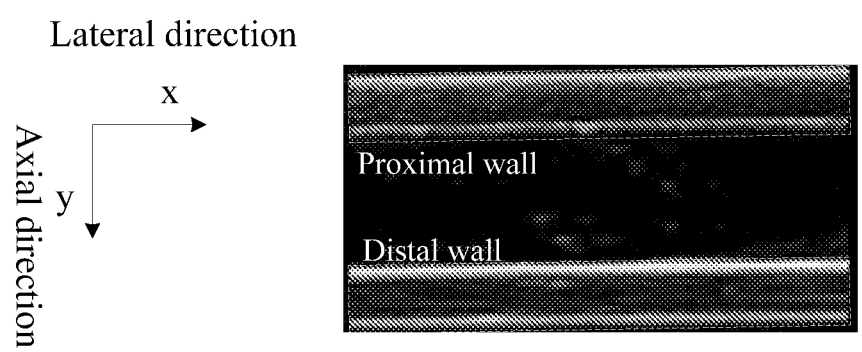
FIG. 7 is an ultrasound B-mode image of the arterial phantom captured by an ultrasound imaging system in accordance with the third embodiment of the present disclosure.
Figure 8:
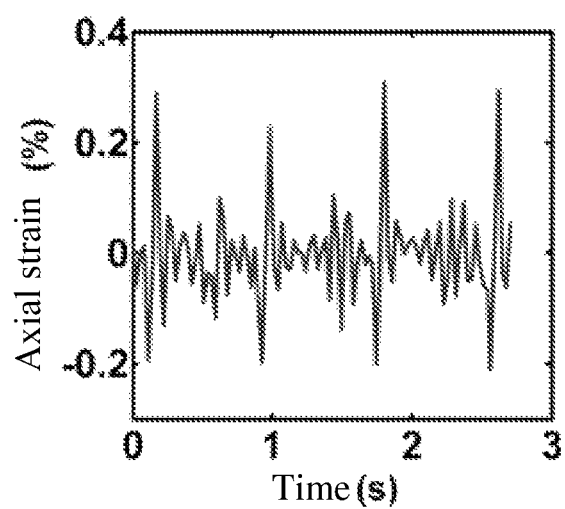
FIG. 8 is axial strain profiles of the arterial phantom (silicone tube) computed over the region of interest (distal wall) shown in FIG. 7 as a function of time.

FIG. 7 is the ultrasound B-mode image of the arterial phantom captured by the ultrasound imaging system; the rectangle indicates the region of interest. In the third embodiment, the arterial phantom 210 is a silicone tube, the internal diameter of the silicone tube is 8 mm, the outer diameter of the silicone tube is 12 mm, its wall thickness is 2 mm. A sequence of 2-D ultrasound B-mode images were acquired at a frame rate of 106 Hz using 256 ultrasound beams with a focal depth of 17 mm and field of view of 35 mm (depth) by 27 mm (width). A final interrogation window of 16×8 (pixels$^2$) is used with an overlap ratio of 0.5 for the texture matching analysis. The axial strain profile of the silicone tube (distal wall) can be obtained and shown in FIG. 8. According to the estimated axial displacement v(x, y, n), the displacement difference $\Delta d$ between an inner layer and an outer layer of the silicone tube in one cardiac cycle can be obtained:

$$\Delta d=v(x,y,n)-v(x+1,y,n)$$

For an arterial phantom with a wall thickness of d, the axial strain is: $\Delta\eta=\max(\Delta d)/d$. The elastic modulus of the wall of the arterial phantom (silicone tube) can be obtained by the following formula:

$$E = \frac{1}{2}(R_i/d + 1)\frac{\Delta P}{\Delta\eta}$$

where $R_i$ is the inner radius of the artery, $\Delta\eta$ is the maximum displacement gradient between the proximal and distal wall during one cardiac cycle. In an embodiment, an elastic modulus of a silicone tube is calculated as 6.63 MPa using the formula above mentioned.

Figure 9:
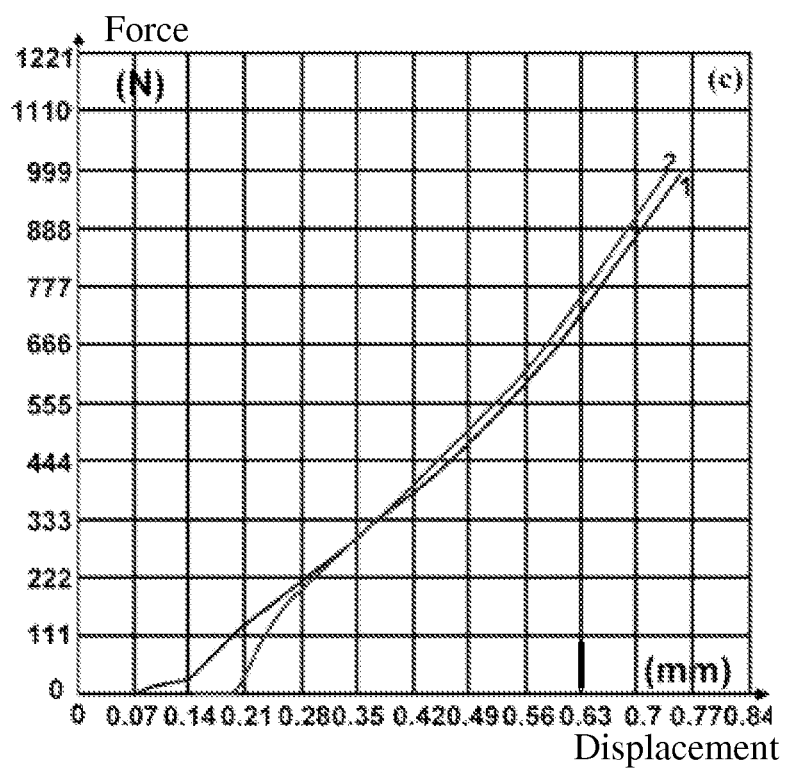
FIG. 9 is a relation curve between force and displacement of two silicone tube samples measuring by an electronic universal material testing machine (CMT6104).

The elastic modulus of the silicone tube is also tested on an electronic universal material testing machine (CMT6104) to validate the calculated elastic modulus using the texture matching method. Two silicone tube samples are tested on the CMT6104. The relation curve between force and displacement is obtained. Referring to FIG. 9, the elastic modulus of sample 1 is 6.31 MPa, and the elastic modulus of sample 2 is 7.82 MPa. The mean elastic modulus of the two samples is to 7.07 MPa, suggesting that there is a difference of 6% between the calculated value and the measured value.

Figure 10:
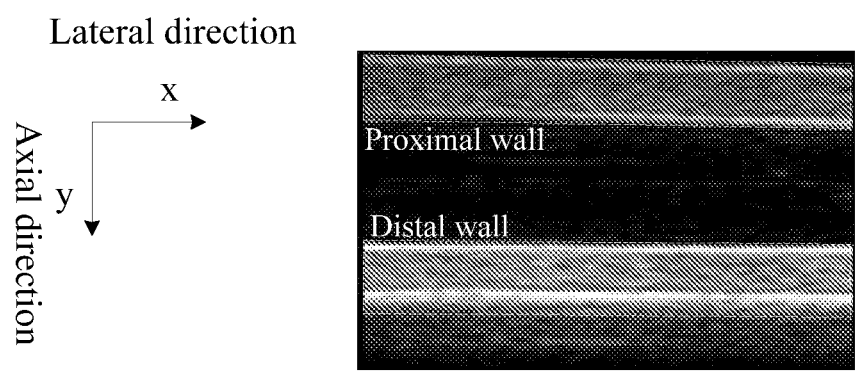
FIG. 10 is an ultrasound B-mode image of an arterial phantom made of polyvinyl alcohol-cryogel (PVA-c) captured by the ultrasound imaging system.
Figure 11:
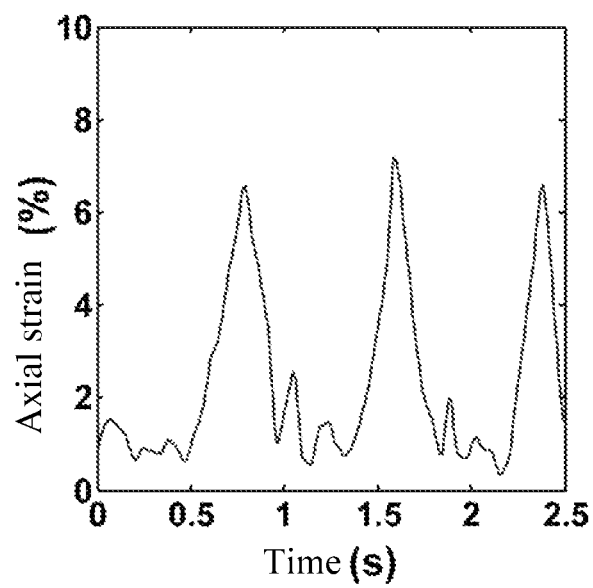
FIG. 11 is axial strain profiles of the arterial PVA-c phantom computed over the region of interest (distal wall) shown in FIG. 10 as a function of time.

An arterial phantom made of polyvinyl alcohol cryogel (PVA-c) could be used instead of the silicone tube, the internal diameter of the PVA-c tube is 6 mm, outer diameter is 12 mm, and wall thickness is 3 mm. The elastic modulus of the arterial phantom made of PVA-c is obtained by the same method to the silicone tube. FIG. 10 is an ultrasound B-mode image of the arterial phantom made of PVA-c captured by the ultrasound imaging system, FIG. 11 is axial strain profiles of the arterial PVA phantom computed over the region of interest (distal wall) shown in FIG. 10 as a function of time. The elastic modulus of the arterial PVA phantom is calculated as 343 kPa, while the elastic modulus of the arterial PVA phantom is 328.8 kPa measured by mechanical method. There is a difference of 4.1% between calculated value and measured value.

Experimental results prove the accuracy and feasibility of the image-based method for measuring elasticity of biological tissues.

The image-based method for measuring elasticity of biological tissues can be applied to various resolutions of grayscale images obtaining in ultrasound imaging, optical imaging, photoacoustic imaging, CT imaging, magnetic resonance imaging etc. The system can be integrated into a traditional clinical imaging system as an image post-processing software module to characterize tissue elasticity. Because it's not necessary to update the traditional clinical imaging system hardware, updating cost is low. It's easy to be accepted by the hospital and is convenient to popularize. In addition, the measurement result is accurate, the calculation time is short, and the cost is low.

The present disclosure also provides an image-based system for measuring elasticity of biological tissues, the system includes:

A grayscale image module, the grayscale image module is configured for obtaining successive N frames of grayscale images of a testing biological tissue, where N is a positive integer.

A region of interest module, the region of interest module is configured for obtaining regions of interest in the grayscale images.

A dividing interrogation window module, the dividing interrogation window module is configured for dividing the region of interest into a grid of small sections.

A relative displacement vector module, the relative displacement vector module is used to calculate relative displacement vector of each interrogation window using texture matching method.

An elastic modulus module, the elastic modulus module is configured for calculating elastic modulus of each interrogation window according to the relative displacement vectors.

In a preferred embodiment, the relative displacement vector calculating module includes:

A translational displacement module, the translational displacement module is configured for obtaining two-dimensional translational displacement of each interrogation window between two successive frames according to two-dimensional normalized cross-correlation technique, sub-pixel method and filter interpolation method.

A geometric transformation displacement module, the geometric transformation displacement module uses a multiple iterative algorithm to estimate rotation and deformation according to the gradient of translational displacement.

A spurious vector elimination module, the spurious vector elimination module is configured for obtaining more accurate displacement estimates, and the relative displacement vectors between the two successive frames.

In a preferred embodiment, the elastic modulus calculating module includes:

A displacement gradient module, the displacement gradient module is configured for obtaining a displacement gradient (strain) of each layer with a constant thickness.

A maximum strain module, the maximum strain module is configured for obtaining maximum strain of each layer during one cardiac cycle.

An elastic modulus module, the elastic modulus module is configured for obtaining the elastic modulus according to the maximum strain and the blood pressure applied normal to each layer.

Although the present invention has been described with reference to the embodiments thereof and the best modes for carrying out the present invention, it is apparent to those skilled in the art that a variety of modifications and changes may be made without departing from the scope of the present invention, which is intended to be defined by the appended claims.

What is claimed is:

1. An image-based method for measuring elasticity of biological tissues, comprising the following steps:
   step A, obtaining a cineloop consisting of N grayscale images of a testing biological tissue, where N is a positive integer; wherein step A further includes
      step A1, collecting successive N grayscale images by an imaging system, where N is the number of image frames collected by the imaging system within m cardiac cycles, where m is a positive integer;
   step B, obtaining regions of interest (ROI) of the grayscale images;
   step C, dividing the regions of interest into a grid of small sections known as interrogation windows;
   step D, calculating a relative displacement vector of each interrogation window using texture matching method; wherein step D further includes
      step D1, calculating the two-dimensional translational displacement of the texture of each interrogation window using the 2-D normalized cross-correlation technique which combines the sub-pixel method and the filter and interpolation method;
      step D2, estimating rotation and deformation according to the gradient of the two-dimensional translational displacement using a multiple iterative algorithm;
      step D3, applying the 2-D normalized cross-correlation technique to a reduced interrogation window to obtain higher spatial resolution based on the rotation and deformation displacements and using a spurious vector elimination algorithm to obtain more accurate displacement estimates; and
   step E, calculating elastic modulus of each interrogation window according to the relative displacement vectors said displacement vectors including lateral and axial components stored in three-dimensional (3-D) arrays, where the three dimensions are lateral and axial positions within an image and frame number.

2. The method according to claim 1, wherein the step E further comprises the following steps:
   step E1, obtaining the displacement gradient of each layer with a constant thickness from the estimated axial displacement;
   step E2, obtaining the maximum displacement gradient of each layer during one cardiac cycle;
   step E3, obtaining the elastic modulus according to the maximum displacement gradient and the blood pressure applied normal to each layer.

3. The method according to claim 1, further comprising:
   slicing the biological tissue into sections;
   pathology staining the section;
   obtaining composition distributions of the biological tissue according to the pathology staining;
   obtaining a range of the elastic modulus of the different compositions according to the distributions of the composition and the elastic modulus.

4. The method according to claim 1, wherein the step E further comprises the following steps:
   step E1, obtaining the displacement gradient of each layer with a constant thickness from the estimated axial displacement;
   step E2, obtaining the maximum displacement gradient of each layer during one cardiac cycle;
   step E3, obtaining the elastic modulus according to the maximum displacement gradient and the blood pressure applied normal to each layer.

5. An image-based system for measuring elasticity of biological tissues, comprising:
   a grayscale image module configured to obtain N successive grayscale images of a testing biological tissue, where N is a positive integer;
   a region of interest module configured to obtain regions of interest in the grayscale images;
   a dividing interrogation window module configured to divide the regions of interest into a grid of small sections;

a relative displacement vector module configured to calculate relative displacement vectors of each interrogation window using texture matching method; said displacement vectors including lateral and axial components stored in three-dimensional (3-D) arrays, where the three dimensions are lateral and axial positions within an image and frame number; and an elastic modulus module configured to calculate elastic modulus of each interrogation window according to the relative displacement vectors;

wherein the grayscale image module is an imaging system, the N successive grayscale images are collected by the imaging system, and N is the number of image frames collected by the imaging system within m complete cardiac cycles, where m is a positive integer; and wherein the relative displacement vectors module comprises:

a translational displacement module configured to obtain two-dimensional translational displacement of each interrogation window between two successive frames according to two-dimensional normalized cross-correlation technique, sub-pixel method and filter interpolation method;

a geometric transformation displacement module configured to use a multiple iterative algorithm to calculate a rotation and a deformation of the biological tissue according to a displacement gradient of the two-dimensional translational displacements;

a spurious vector elimination module configured to obtain more accurate displacement estimates and the relative displacement vectors between the two successive frames.

6. The system according to claim 5, wherein the elastic modulus calculating module comprises:

a displacement gradient module configured to obtain a displacement gradient of each layer with a constant thickness;

a maximum displacement gradient module configured to obtain the maximum displacement gradient of each layer during one cardiac cycle;

an elastic modulus module configured to obtain the elastic modulus according to the maximum displacement gradient and the blood pressure applied normal to each layer.

7. An image-based system for measuring elasticity of biological tissues, comprising:

a grayscale image module configured to obtain N successive grayscale images of a testing biological tissue, where N is a positive integer;

a region of interest module configured to obtain regions of interest in the grayscale images;

a dividing interrogation window module configured to divide the regions of interest into a grid of small sections;

a relative displacement vector module configured to calculate relative displacement vectors of each interrogation window using texture matching method; said displacement vectors including lateral and axial components stored in three-dimensional (3-D) arrays, where the three dimensions are lateral and axial positions within an image and frame number; and an elastic modulus module configured to calculate elastic modulus of each interrogation window according to the relative displacement vectors;

wherein the grayscale image module is an imaging system, the N successive grayscale images are collected by the imaging system, and N is the number of image frames collected by the imaging system within m complete cardiac cycles, where m is a positive integer; and wherein the elastic modulus calculating module comprises:

a displacement gradient module configured to obtain a displacement gradient of each layer with a constant thickness;

a maximum displacement gradient module configured to obtain the maximum displacement gradient of each layer during one cardiac cycle;

an elastic modulus module configured to obtain the elastic modulus according to the maximum displacement gradient and the blood pressure applied normal to each layer.

\* \* \* \* \*